(12) United States Patent
Chen et al.

(10) Patent No.: US 9,938,319 B2
(45) Date of Patent: Apr. 10, 2018

(54) EGG WHITE PROCESSING

(71) Applicant: Synageva BioPharma Corp., Lexington, MA (US)

(72) Inventors: Liang Chen, San Diego, CA (US); Markley C. Leavitt, Lexington, MA (US); Michael Titus, Lexington, MA (US)

(73) Assignee: ALEXION PHARMACEUTICALS, INC., New Haven, CT (US)

( * ) Notice: Subject to any disclaimer, the term of this patent is extended or adjusted under 35 U.S.C. 154(b) by 208 days.

(21) Appl. No.: 14/691,817

(22) Filed: Apr. 21, 2015

(65) Prior Publication Data

US 2015/0307547 A1 Oct. 29, 2015

Related U.S. Application Data

(60) Provisional application No. 61/983,003, filed on Apr. 23, 2014.

(51) Int. Cl.
*C07K 1/36* (2006.01)

(52) U.S. Cl.
CPC ..................................... *C07K 1/36* (2013.01)

(58) Field of Classification Search
None
See application file for complete search history.

(56) References Cited

U.S. PATENT DOCUMENTS

| | | |
|---|---|---|
| 2,168,926 A | 8/1939 | Littlefield et al. |
| 2,191,257 A | 2/1940 | Littlefield et al. |
| 2,237,087 A | 4/1941 | Littlefield et al. |
| 2,377,961 A | 6/1945 | Pollak |
| 2,427,726 A | 9/1947 | Hopkins et al. |
| 2,610,918 A | 9/1952 | Kline et al. |
| 2,744,829 A * | 5/1956 | Shaffer ................... A23L 15/30 426/32 |
| 2,758,935 A | 8/1956 | Shaffer |
| 5,780,593 A | 7/1998 | Lihme et al. |
| 2009/0299037 A1* | 12/2009 | Chen ................... C07K 14/505 530/351 |
| 2009/0307786 A1 | 12/2009 | Rapp et al. |
| 2011/0033440 A1 | 2/2011 | Strohbehn et al. |

FOREIGN PATENT DOCUMENTS

| | | |
|---|---|---|
| EP | 0188262 | 7/1986 |
| EP | 0179946 | 6/1988 |
| EP | 0352437 | 6/1994 |
| EP | 0482228 | 6/1996 |
| WO | 1997/31947 | 9/1997 |
| WO | 2003/099041 | 12/2003 |
| WO | 2005/074703 | 8/2005 |
| WO | 2012/003322 | 1/2012 |
| WO | 2012/146716 | 11/2012 |

OTHER PUBLICATIONS

International Preliminary Report on Patentability in International Application No. PCT/US2015/026794, dated Nov. 3, 2016, 10 pages.
International Search Report and Written Opinion issued in PCT/US2015/26794 dated Aug. 14, 2015 (13 pages).
English translations of Office Action issued in corresponding Colombian Application No. NC2016/0003573 dated Dec. 8, 2016 (3 pages).

* cited by examiner

*Primary Examiner* — Suzanne M Noakes
*Assistant Examiner* — Stephen M Chong
(74) *Attorney, Agent, or Firm* — Medler Ferro Woodhouse & Mills

(57) ABSTRACT

This disclosure relates to inexpensive and efficient methods of preparing egg white (e.g., obtained from eggs laid by transgenic chickens) for bulk chromatographic isolation of proteins (e.g., recombinant proteins) from the egg white, as well as methods of filtering acidified egg white and methods of isolating proteins from the egg white.

48 Claims, No Drawings

EGG WHITE PROCESSING

CROSS-REFERENCE TO RELATED APPLICATION

This application claims priority to U.S. Provisional Application No. 61/983,003, filed on Apr. 23, 2014, the contents of which are hereby incorporated by reference in their entirety.

BACKGROUND

Transgenic avians (e.g., transgenic chickens, quails or turkeys) are a desirable expression system for obtaining exogenous recombinant proteins for use in pharmaceutical or other commercial applications that require large amounts of protein supply. A hen can lay up to 330 eggs per year, each containing 6.5 grams of protein. About 3.5 grams of the total protein is from egg white, of which 90% is accounted for by seven different proteins; the ovalbumin alone accounts for 2 grams of egg white protein (about 50% of the egg white protein). Currently, the average exogenous gene product derived from oviduct specific expression of a transgene and recovered from the egg white is known to be about 5-10 mg per egg. Advantages of exogenous protein production in chicken eggs include short generation times and prolific rates of reproduction via artificial insemination. Various proteins have been expressed in eggs of transgenic chickens. See, e.g., U.S. Pat. No. 6,730,822 and U.S. Publication No. 2006/0015960.

Many exogenous therapeutic proteins (e.g., recombinant human proteins such as cytokines (e.g., erythropoietin, granulocyte colony-stimulating factor (GC-SF), interferons, and granulocyte-macrophage colony-stimulating factor (GM-CSF)), antibodies, and various human lysosomal enzymes) are of interest to the pharmaceutical industry. The therapeutic proteins can readily be obtained in significant quantities from, for example, egg white of transgenic chickens. Traditional methods of isolating exogenous proteins from the egg white, however, often rely on use of immunoaffinity procedures or other procedures only suitable for small scale production (e.g., involving total egg white volume of 5 L at most). For a large-scale protein production, such a procedure is not practical based on costs, labor, and time.

SUMMARY

This disclosure is based on the unexpected discovery that adding a small amount of an acidic buffer (e.g., in a single bolus injection) to a pool of egg white (e.g., obtained from eggs laid by transgenic avian such as chickens, quails and turkeys) of industrial scale (e.g., having a volume of at least 10 liters) can prepare the egg white for bulk chromatographic isolation of recombinant proteins such as human therapeutic proteins from the egg white without the need of diluting the egg white. Such a method can significantly reduce the amount of egg white materials subject to the downstream isolation/purification processes (e.g., the amount of the columns used in chromatographic isolation), thereby significantly reducing the costs, labor, and time of isolating recombinant proteins from egg white. Accordingly, the methods described in the present disclosure can greatly improve the efficiency of egg white preparation for a large, industrial scale of therapeutic protein production.

In one aspect, this disclosure features a method of preparing egg white for bulk chromatographic processing that includes the steps of: (1) adding an acidic buffer comprising an acidic agent to a pool of egg white, the acidic buffer being from about 0.5 wt % to about 5 wt % per kilogram of the egg white; and (2) mixing the acidic buffer and the egg white to form a mixed egg white having a pH of from about 5 to about 6.5.

In another aspect, this disclosure features a method of isolating a recombinant protein from egg white that includes the steps of: (1) providing a pool of egg white containing a recombinant protein, the pool having a volume of at least about 10 liters; (2) adjusting the pH of the egg white to from about 5 to about 6.5, in which the conductivity of the pH-adjusted egg white is from about 8 mS/cm to about 20 mS/cm; (3) filtering the egg white to form a solution (i.e., a clear solution); and (4) isolating the recombinant protein in the egg white by column chromatography.

In still another aspect, this disclosure features a method of filtering acidified egg white that includes the steps of: (1) passing a pre-treatment buffer having a conductivity between about 8 mS/cm and about 20 mS/cm through a filter; and (2) passing egg white having a pH from about 5 to about 6.5 through the filter to obtain a filtered egg white.

Embodiments can include one or more of the following features.

The acidic agent can be selected from the group consisting of acetic acid, hydrochloric acid, sulfuric acid, nitric acid, phosphoric acid, hydrofluoric acid, hydrobromic acid, perchloric acid, citric acid, boric acid, tartaric acid, lactic acid, formic acid, oxalic acid, uric acid, and barbituric acid.

The acidic buffer can further include from about 5M to about 6M (e.g., about 5.7 M) sodium acetate.

The acidic buffer can be from about 0.5 wt % to about 2 wt % (e.g., from about 0.7 wt % to about 1.5 wt %, from about 0.9 wt % to about 1.4 wt %, or from about 1.2 wt % to about 1.3 wt %) per kilogram of the egg white.

The acidic buffer can have a pH from about 4 to about 6.5 (e.g., about 4, about 4.5, about, 5, about 5.5, about 6.0 or about 6.5).

After mixing the acidic buffer with the egg white, the pH of the mixed egg white can be from about 5 to about 6.5. In some embodiments, the pH of the mixed egg white is from 5 to about 6.3 (e.g., from about 5.7 to about 6.3, from about 5.8 to about 6.2, from about 5.9 to about 6.1, or about 6). In some embodiments, the pH of the mixed egg white is a value such that the mixed egg white is rendered least viscous.

The egg white can be mixed for at least about 1 hour and/or at a temperature from about 2° C. to about 25° C.

The egg white pool can have a volume of at least about 10 liters (e.g., at least about 50 liters).

The acidic buffer can be added to the egg white pool in a single bolus injection and/or at a rate of at least about 1 L/minute.

The addition of the acidic buffer to the egg white and the mixing of the egg white can be performed concurrently.

The method can further include a step of allowing the mixed egg white to settle such that the egg white separates into top, middle and bottom layers. In such embodiments, the method can further include a step of isolating the middle layer. In some embodiments, the method can further include filtering the middle layer after the isolation step. The filtering can include passing at least a portion (e.g., all) of the middle layer through a filter having an average pore size ranging from about 0.1 μm to about 100 μm. In some embodiments, the filtering can include passing at least a portion of the middle layer through a plurality of filters.

The method can further include filtering the mixed egg white without allowing the mixed egg white to settle. In such embodiments, the filtering step can include filtering the mixed egg white through a filter having an average pore size ranging from about 0.1 μm to about 100 μm. In some embodiments, the filtering step can include one or more subsequent filtering steps following an initial filtering of the mixed egg white, the one or more subsequent filtering steps using one or more filters having an average pore size ranging from about 0.1 μm to about 40 μm.

The method can further include a centrifugation step after the mixing step, in which the mixed egg white is centrifuged to separate precipitates containing ovomucin-lysozyme complexes from supernatant.

The egg white can include a recombinant therapeutic protein exogenous to egg white.

The acidic buffer can have a conductivity from about 8 mS/cm to about 40 mS/cm.

The acidic buffer can be from about 0.5 wt % to about 5 wt % per kilogram of the egg white.

A pre-treatment buffer can be used to prepare filters for passing acidified egg white. The pretreatment buffer can have a pH substantially similar to or the same as the pH of the egg white, ranging from about 5.0 to about 6.5. For example, the pre-treatment buffer can have a pH from about 5.9 to about 6.1 (e.g., about 6).

The pre-treatment buffer can include sodium phosphate and sodium chloride.

The pre-treatment buffer can have a conductivity from about 10 mS/cm to about 20 mS/cm.

The acidified egg white can have a conductivity from about 8 mS/cm to about 20 mS/cm.

The filter can have a filtration medium area of at least about 8 m².

The filter can have an average pore size from about 0.1 μm to about 100 μm.

The egg white can be passed through the filter under a differential pressure less than about 30 psi (e.g., less than about 15 psi).

Embodiments can have the following advantages.

In general, chromatographic columns used in isolation/purification of exogenous protein from egg white are very costly, which can be one of the key limiting factors in commercial and industrial scale production of recombinant proteins from egg white. Because only a small amount of an acidic buffer is used to obtain acidified egg white, the amount of the acidified egg white used to obtain purified therapeutic proteins is significantly reduced (i.e., at least 3 to 4-fold less than conventional dilution methods). As a result, time consumed for loading the acidified egg white to the subsequent columns is also significantly reduced, which permits rapid protein production in an industrial process. In addition, because some therapeutic proteins are sensitive to the environment exposed during the egg white preparation and isolation/purification processes, minimizing the time spent in the preparation and isolation/purification processes by reducing sample volume is highly advantageous for commercial production that typically involves an egg white volume of 500 L or more. In sum, processing time, materials and labor can be greatly minimized by using the methods described herein.

Other features, objects, and advantages will be apparent from the description and drawings, and from the claims.

DETAILED DESCRIPTION

This disclosure relates to efficient methods of preparing egg white (e.g., obtained from eggs laid by transgenic chickens) for bulk chromatographic isolation of proteins (e.g., recombinant proteins) from the egg white, as well as methods of isolating proteins from the egg white. The egg white prepared by the methods described herein is generally in the form a homogeneous, low viscosity solution that is suitable for bulk chromatographic processing.

In some embodiments, egg white used as a starting material of the methods described herein can include a recombinant protein (e.g., a recombinant therapeutic protein) exogenous to the egg white. Exemplary recombinant proteins include cytokines such as GC-SF, GM-CSF, erythropoietin, and interferons such as interferon-α or interferon-β; human lysosomal enzymes; immunoglobulins (e.g., antibodies); and structural proteins. Other exemplary recombinant proteins that can be isolated from bulk chromatographic processing have been described, e.g., in U.S. Application Publication No. 2009/0299037.

In general, the methods of preparing egg white described herein include (1) adding an suitable amount of an acidic buffer (e.g., from about 0.5 wt % to about 5 wt % per kilogram of the egg white) containing an acidic agent to a pool of egg white (e.g., having a volume of at least about 10 liters); and (2) mixing the acidic buffer and the egg white to form a mixed egg white having a suitable pH (e.g., a pH ranging from about 5 to about 6.5).

In general, the egg white pool used in the methods described herein is at an industrial scale and has a relatively large volume. For example, the egg white pool can have a volume of at least about 10 liters (e.g., at least about 50 liters, at least about 100 liters, at least about 200 liters, at least about 300 liters, at least about 400 liters, at least about 500 liters, at least about 600 liters, at least about 700 liters, at least about 800 liters, at least about 900 liters, at least about 1,000 liters, at least about 1,500 liters, at least about 2,000 liters, at least about 3,000 liters, at least about 4,000 liters, at least about 5,000 liters, at least about 10,000 liters, or at least about 20,000 liters). Methods of preparing egg white as a starting material to be used in the methods described herein have been described, e.g., in U.S. Application Publication No. 2009/0299037.

The acidic agent in the acidic buffer can generally be any suitable acid (e.g., an organic acid or an inorganic acid). Exemplary acidic agents include acetic acid, hydrochloric acid, sulfuric acid, nitric acid, phosphoric acid, hydrofluoric acid, hydrobromic acid, perchloric acid, citric acid, boric acid, tartaric acid, lactic acid, formic acid, oxalic acid, uric acid, and barbituric acid. In some embodiments, a combination of two or more (e.g., three or four) acids can be used as the acidic agent in the acidic buffer.

In some embodiments, the acidic buffer can include one or more salts (e.g., alkaline salts). An example of such a salt can be sodium acetate. In some embodiments, the salt used in the acidic buffer can be a salt of the acidic agent used in the acidic buffer. In other embodiments, the salt used in the acidic buffer can be a salt of an acid different from the acidic agent used in the acidic buffer. In some embodiments, the acidic buffer can include from about 5M to about 6M (e.g., about 5.7 M) of a salt (e.g., sodium acetate). Without wishing to be bound by theory, it is believed that using a salt having such a concentration can result in an acidic buffer having a suitable amount of buffering content. If the buffering content is too high, the acidic buffer may become flammable and/or corrosive, rendering the buffer unsafe to maintain, handle, and/or store. If the buffering content is too low, a larger volume of the acidic buffer might be needed to adjust the pH of the egg white to the target value, thereby reducing the efficiency of the egg white preparation process, as well as the downstream protein isolation/purification processes.

In general, the amounts of the acidic agent and the salt used in the acidic buffer can vary depending on the desired pH of the acidic buffer. In some embodiments, the acidic buffer can have a pH from about 4 to about 6.5 (e.g., from about 4 to about 5 or from about 4 to about 4.5). For example, the acidic buffer can have a pH of about 4 or a pH of about 4.5.

The acidic buffer can be formed by any suitable methods known in the art. For example, the acidic buffer can be formed by adding an acidic agent to a solution containing a base to adjust the pH of the solution to a desired value. For example, glacial acetic acid solution can be added to an appropriate amount of NaOH to obtain an acidic buffer containing 5.7M sodium acetate.

In general, the amount of the acidic buffer relative to that of the egg white is small. For example, the acidic buffer can be from about 0.5 wt % to about 5 wt % (e.g., from about 0.5 wt % to about 2 wt %, from about 0.7 wt % to 1.5 wt %, from about 0.9 wt % to about 1.4 wt %, from about 1 wt % to about 1.4%, or from about 1.1 wt % to about 1.3 wt %) per kilogram of the egg white. Conventionally, efforts to create a homogeneous, low viscosity egg white suitable for bulk chromatographic processing requires adding an acidic buffer having a volume 2- to 5-fold (i.e., 200% to 500%) of the volume of the egg white as it was not expected that adding a small amount of an acidic buffer would be effective in adjusting the pH of the egg white to the target value. Such a process is not economically practical or feasible at a large manufacturing scale due to the size constraints of chromatographic columns and other manufacturing equipment used in the egg white preparation process. Unexpectedly, the present inventors discovered that a homogeneous, low viscosity egg white suitable for bulk chromatographic processing can be obtained by adding a small amount of an acidic buffer (e.g., at most about 5 wt % per kilogram of egg white) relative to the amount of egg white, thereby significantly reducing the amount of the columns used in the chromatographic isolation processes, the sizes of other equipment used in these processes, and the cost and time of isolating recombinant proteins from egg white.

Without wishing to be bound by theory, it is believed that additional advantages of adding a relatively smaller amount of an acidic buffer relative to the amount of egg white include (1) negligible dilution of egg white, (2) essentially no change in conductivity, which allows for the precipitation of ovomucin-lysozyme complexes from egg white, which in turn reduces the viscosity of the egg white at lower pH range (e.g., pH 5-6.5) and facilitates separation of unwanted materials from the egg white during the filtration and chromatographic processes, and (3) minimizing formation of low pH pockets within the viscous egg white that can potentially damage recombinant proteins or result in uneven pH of the egg white materials.

In general, the acidic buffer can have a conductivity ranging from about 8 mS/cm to about 40 mS/cm. For example, the acidic buffer can have a conductivity of at least about 8 mS/cm (e.g., at least about 9 mS/cm, at least about 10 mS/cm, at least about 11 mS/cm, at least about 12 mS/cm, at least about 13 mS/cm, at least about 14 mS/cm, at least about 15 mS/cm, at least about 16 mS/cm, at least about 17 mS/cm, at least about 18 mS/cm, at least about 19 mS/cm, at least about 20 mS/cm, at least about 21 mS/cm, at least about 22 mS/cm, at least about 23 mS/cm, at least about 24 mS/cm, at least about 25 mS/cm) and/or at most about 40 mS/cm (e.g., at most about 39 mS/cm, at most about 38 mS/cm, at most about 37 mS/cm, at most about 36 mS/cm, at most about 35 mS/cm, at most about 34 mS/cm, at most about 33 mS/cm, at most about 32 mS/cm, at most about 31 mS/cm, at most about 30 mS/cm, at most about 29 mS/cm, at most about 28 mS/cm, at most about 27 mS/cm, at most about 26 mS/cm, or at most about 25 mS/cm). For example, the acidic buffer can have a conductivity of any value between about 8 mS/cm and about 40 mS/cm. Without wishing to be bound by theory, it is believed that using an acidic buffer having a conductivity from about 8 mS/cm to about 40 mS/cm would minimize the changes to the conductivity of the mixed egg white so that the process can be implemented and streamlined with the downstream protein isolation step without changing the isolation conditions of the column chromatography used in the isolation step and without causing further precipitation or aggregation.

In some embodiments, the acidic buffer can be added to the egg white pool in a single bolus injection. In some embodiment, the single bolus injection is performed at a suitable injection rate (e.g., at least about 1 L/minute) to ensure that the addition of the acidic buffer is added within a suitable amount of time (e.g., at most about 5 minutes). Without wishing to the bound by theory, it is believed that the advantages of using a single bolus injection include (1) forming relatively large flocculent that settles easily under gravity, thereby reducing the need for large filters and (2) avoiding the need for continuous titration of a viscous egg white pool, which can cause false pH readings that trigger repeated addition of an acid or a base, which in turn can potentially damage the recombinant proteins in the egg white and increase the turbidity of the egg white solution produced.

In some embodiments, after the acidic buffer is added to the egg white pool, the egg white is mixed at a suitable temperature (e.g., from about 2° C. to about 25° C.) for a suitable period of time (e.g., at least about 1 hour) to form a mixed egg white having a suitable pH. In some embodiments, the addition of the acidic buffer and the mixing of the egg white are performed concurrently.

In general, the addition of the acidic buffer and the mixing of the acidic buffer with the egg white result in formation of a large amount of precipitates (e.g., ovomucin-lysozyme complexes). The precipitates generally reduce the viscosity of the egg white remaining in the solution.

In some embodiments, the pH of the mixed egg white is a value such that the mixed egg white is rendered least viscous. For example, the mixed egg white can have a pH at least about 5 (e.g., at least about 5.2, at least about 5.4, at least about 5.6, at least about 5.7, at least about 5.8 or at least about 5.9) and/or at most about 6.5 (e.g., at most about 6.3, at most about 6.2 or at most about 6.1). In some embodiments, the mixed egg white can have a pH of about 6. Without wishing to be bound by theory, it is believed that such a pH (e.g., about 6) can allow formation of the largest amount of precipitates from egg white that settle under gravity, thereby reducing the need for filtration and facilitating formation of a homogeneous, low viscosity egg white solution.

In general, the mixed egg white (i.e., the acidified or pH adjusted egg white) has a relative low conductivity (e.g., similar to the conductivity of an egg white not treated with an acidic buffer). For example, the mixed egg white can have a conductivity of at least about 8 mS/cm (e.g., at least about 8.2 mS/cm, at least about 8.4 mS/cm, at least about 8.6 mS/cm, at least about 8.8 mS/cm, at least about 9 mS/cm, at least about 9.2 mS/cm, at least about 9.4 mS/cm, at least about 9.6 mS/cm, at least about 9.8 mS/cm, at least about 10 mS/cm, at least about 11 mS/cm, at least about 12 mS/cm, at least about 13 mS/cm, or at least about 14 mS/cm) and/or at most about 20 mS/cm (e.g., at most about 19 mS/cm, at most about 18 mS/cm, at most about 17 mS/cm, at most about 16 mS/cm, at most about 15 mS/cm, at most about 14 mS/cm, at most about 13 mS/cm, at most about 12 mS/cm, at most about 11.8 mS/cm, at most about 11.6 mS/cm, at most about 11.4 mS/cm, at most about 11.2 mS/cm, at most about 11 mS/cm, at most about 10.8 mS/cm, at most about 10.6 mS/cm, at most about 10.4 mS/cm, at most about 10.2 mS/cm, or at most about 10 mS/cm). For example, the mixed egg white can have a conductivity of any value between about 8 mS/cm and about 20 mS/cm. Without wishing to be bound by theory, it is believed that keeping the mixed egg white at conductivity from about 8 mS/cm to about 20 mS/cm would allow the mixed egg white to comply with the conditions used in the downstream protein isolation step so that the mixed egg white can be consistently used in the isolation step without changing the isolation conditions of the column chromatography used in this step.

After the mixing is completed, the methods described herein can include an optional step of allowing the mixed egg white to settle for a suitable period of time (e.g., at least about 6 hours) such that the egg white separates into top, middle and bottom layers. Typically, the top layer includes certain unwanted materials (e.g., denatured protein and foamy lipids including phospholipids, triglyceride, and cholesterol) having a low density, the bottom layer includes the precipitates formed from the egg white proteins (e.g., ovomucin-lysozyme complexes), and the middle layer includes a relatively clear egg white solution.

In some embodiments, during the settling step, if the pH of the mixed egg white becomes falling outside the desired value (e.g., 5.7±0.1, 6.0±0.1, or 6.3±0.1), it can be adjusted to reach the desired value by using an acid (e.g., the acidic buffer described above) or a base (e.g., a 5.7 M sodium acetate or 1 N sodium hydroxide solution). In such embodiments, the pH adjustment can be followed by additional mixing (e.g., for at least about 1 hour) and settling (e.g., for at least about 3 hours) at room temperature. In general, the total mixing and settling time does not exceed 24 hours to minimize the time that the exogenous proteins in the egg white are exposed to the processing environment, thereby maintaining the biological activities of these proteins.

In some embodiments, the methods described herein can include a step of isolating the middle layer from the mixed egg white after the setting step. In general, the middle layer can be isolated by using methods known in the art. For example, the middle layer can be siphoned out of the vessel containing the mixed egg white by inserting a tube (e.g., a metal or polycarbonate tube) into the middle layer (preferably in the center of the middle layer) so that the content of the middle layer can be pumped into a receiving vessel without disturbing the top and bottom layers.

In general, after the middle layer is isolated, at least a portion of the middle layer (e.g., all of the middle layer) can be filtered to remove any particles suspended in the middle layer to obtain a homogeneous, low viscosity, clear egg white solution. This step is also known as egg white clarification. In some embodiments, the middle layer can be filtered through one or more filters having an average pore size at most about 100 µm (e.g., at most about 90 µm, at most about 80 µm, at most about 70 µm, at most about 60 µm, at most about 50 µm, at most about 40 µm, at most about 30 µm, at most about 20 µm, at most about 10 µm, at most about 9 µm, at most about 8 µm, at most about 7 µm, at most about 6 µm, at most about 5 µm, at most about 4 µm, at most about 3 µm, at most about 2 µm, or at most about 1 µm) and/or at least about 0.1 µm (e.g., at least about 0.2 µm, at least about 0.3 µm, at least about 0.4 µm, at least about 0.5 µm, at least about 0.6 µm, at least about 0.7 µm, at least about 0.8 µm, at least about 0.9 µm, at least about 1 µm, at least about 2 µm, or at least about 3 µm). For example, the filter can have an average pore size ranging from about 0.1 µm to about 100 µm (e.g., from about 0.1 µm to about 40 µm, from about 40 µm to about 100 µm, from about 3 µm to about 6 µm, or from about 0.1 µm to about 0.3 µm).

In some embodiments, the middle layer can be filtered through a plurality of filters serially connected to each other, in which the average pore size of the filters decreases sequentially. For example, the middle layer can be filtered through a filtration system containing three serially connected filters, in which the first filter can have an average pore size of about 40 µm, the second filter can have an average pore size from about 3 µm to about 6 µm, and the third filter can have an average pore size from about 0.1 µm to about 0.3 µm. An example of such a filtration system is a system containing sequential depth filters commercially available from Pall Corporation (e.g., containing T2600, K200P and Bio10 depth filters). Optionally, the filtration system can further include a fourth filter (e.g., having an average pore size about 0.2 µm) downstream of the third filter. An example of the fourth filter is a Sartobran P filter available from Sartorius Corporation.

In some embodiments, the filters used to filter the middle layer can have a large filtration medium area. For example, the filters can have a filtration medium area of at least about 1 m$^2$ (e.g., at least about 2 m$^2$, at least about 4 m$^2$, at least about 6 m$^2$, or at least about 8 m$^2$).

In some embodiments, after the acidic buffer and the egg white are mixed to form a mixed egg white, the mixed egg white can be filtered without the need to allow the precipitates in the mixed egg white to settle. In such embodiments, the mixed egg white (including the precipitates formed during the addition/mixing steps and the remaining egg white solution) can be filtered without any prior separation of the precipitates from the mixed egg white. For example, after the acidic buffer and the egg white are mixed, the mixed egg white can be filtered without settling by using one or more filters described herein (e.g., a filtration system containing three serially connected filters having decreasing pore sizes). Without wishing to be bound by theory, it is believed that, by eliminating a settling step, such a method can significantly reduce the time and costs for preparing egg white for bulk chromatographic processing and for isolating proteins from the egg white.

In some embodiments, after the acidic buffer and the egg white are mixed to form a mixed egg white, the mixed egg white can be centrifuged to separate precipitates (e.g., ovomucin-lysozyme complexes) from the supernatant. The supernatant thus obtained can then be filtered by using one or more filters described herein.

In general, the filtered egg white solution can be used to isolate recombinant proteins by using column chromatography, such as ion exchange chromatography or chromatography based on hydrophobic interaction. Examples of such chromatographic methods have been described, e.g., in U.S. Application Publication No. 2009/0299037.

In some embodiments, this disclosure features methods of isolating a recombinant protein from egg white. For example, such methods can include the steps of: (1) providing a pool of egg white containing a recombinant protein, the pool having a volume of at least about 10 liters; (2) adjusting the pH of the egg white to from about 5 to about 6.5, wherein the conductivity of the pH-adjusted egg white is from about 8 mS/cm to about 20 mS/cm; (3) filtering the egg white to form a solution; and (4) isolating the recombinant protein in the egg white by column chromatography. The adjusting step can be performed by adding a small amount of an acidic buffer (e.g., from about 0.5 wt % to about 5 wt % per kilogram of the egg white) to the egg white in the same manner as described above. The filtering and isolating steps can be performed by the methods described herein or methods known in the art.

In some embodiments, this disclosure features methods of filtering acidified egg white (e.g., egg white acidified by an acidic buffer described above). For example, such methods can include the steps of: (1) passing a pre-treatment buffer having a conductivity between about 8 mS/cm and about 20 mS/cm through a filter; and (2) passing egg white (e.g., having a volume of at least about 50 L) having a pH from about 5 to about 6.5 through the filter to obtain a filtered egg white. The filtered egg white can then be used to isolate recombinant proteins by using column chromatography. In some embodiments, the filter used in such methods can be similar to or the same as those described above. For example, the filter can have the same average pore size (e.g., from about 0.1 μm to about 100 μm) or filtration medium area as those described above (e.g., at least about 8 m$^2$).

In some embodiments, the pre-treatment buffer can be used to wet the filter prior to passing the egg white (e.g., acidified egg white). The pre-treatment buffer can include one or more salts (e.g., alkaline salts). Exemplary salts include sodium phosphate and sodium chloride. In some embodiments, the pre-treatment buffer can include a combination of sodium phosphate and sodium chloride.

In general, the pre-treatment buffer can include an acid. Exemplary acids include acetic acid, hydrochloric acid, sulfuric acid, nitric acid, phosphoric acid, hydrofluoric acid, hydrobromic acid, perchloric acid, citric acid, boric acid, tartaric acid, lactic acid, formic acid, oxalic acid, uric acid, and barbituric acid. In some embodiments, a combination of two or more (e.g., three or four) acids can be used in the pre-treatment buffer.

In some embodiments, the pre-treatment buffer can have a pH substantially the same as the pH of the egg white. For example, the pre-treatment buffer can have a pH at least about 5 (e.g., at least about 5.2, at least about 5.4, at least about 5.6, at least about 5.7, at least about 5.8 or at least about 5.9) and/or at most about 6.5 (e.g., at most about 6.4, at most about 6.3, at most about 6.2 or at most about 6.1). In some embodiments, the pre-treatment buffer can have a pH of about 6. Without wishing to be bound by theory, it is believed that using a pre-treatment buffer having a pH substantially the same as the pH of the egg white to treat a filter can adjust the pH of the filter surface to be similar to the pH of the egg white, thereby minimizing precipitation of the egg white during filtration, which can cause blockage in the filter or obstruct the flow of the samples that causes shear stress on the filter, thereby seriously shortening the usage life of the filter.

Generally, the pre-treatment buffer can have a conductivity compatible with the conductivity of the egg white such that the filtered acidified egg white is compatible with the characteristics of the column chromatography (e.g., ion exchange chromatography) used in the downstream isolation/purification processes. For example, the pre-treatment buffer can have a conductivity of at least about 8 mS/cm (e.g., at least about 9 mS/cm, at least about 10 mS/cm, at least about 11 mS/cm, at least about 12 mS/cm, at least about 13 mS/cm, at least about 14 mS/cm, at least about 15 mS/cm, at least about 16 mS/cm, at least about 17 mS/cm, at least about 18 mS/cm) and/or at most about 20 mS/cm (e.g., at most about 19 mS/cm, at most about 18 mS/cm, at most about 17 mS/cm, at most about 16 mS/cm, at most about 15 mS/cm, at most about 14 mS/cm, at most about 13 mS/cm, at most about 12 mS/cm, or at most about 11 mS/cm). For example, the pre-treatment buffer can have a conductivity of any value between about 8 mS/cm and about 20 mS/cm. The present inventors found that using a filter without being treated with the above pre-treatment buffer to filter an egg white solution would cause the filter to be clogged rapidly by the precipitates formed during the filtration process. On the other hand, the present inventors found unexpectedly that using a pre-treatment buffer having the above conductivity to treat a filter can adjust the conductivity of the filter surface to be similar to that of the egg white, thereby minimizing precipitation of the egg white during filtration and significantly increasing the life time of the filter.

In some embodiments, the egg white can be passed through a filter under a relatively small differential pressure (e.g., less than about 30 psi, less than about 25 psi, less than about 20 psi, less than about 15 psi, less than about 12 psi, less than about 10 psi, or less than about 5 psi). Without wishing to be bound by theory, it is believed that passing the egg white through a filter under a relatively small differential pressure can minimize damages and/or blockage to the filter, thereby reducing product costs as the filter can be very expensive.

The contents of all publications cited herein (e.g., patents, patent application publications, and articles) are hereby incorporated by reference in their entirety.

The following examples are illustrative and not intended to be limiting.

Example 1

Method of Preparing Egg White for Bulk Chromatographic Processing Having a Settling Step Fifty to four hundred kilograms of frozen egg white stored at −20° C. in 4 L Nalgene bottles was thawed at room temperature in water baths set to 21±1° C. for approximately 5-7 hours. Once every hour, each bottle was removed from the water bath, visually inspected to determine degree of thaw, inverted repeatedly and placed back into the water bath until the thaw was complete. Thawed bottles were removed from the water baths and stored at 2-8° C. After the last egg white bottle was thawed, the egg white in the bottles was pooled into an open top mixing vessel. An acidic buffer containing 5.7 M sodium acetate at pH 4.0 (about 1.3% wt/wt with respect to the weight of the egg white) was added to the thawed egg white pool at 1 kilogram per minute, ensuring that the duration of the addition of the acidic buffer did not exceed 5 minutes, to obtain a final target pH of 6.0±0.1 at 2-8° C. The egg white mixture was stirred continuously for 1 hour in the open top mixing vessel without temperature control, and then decanted into a closed single use mixer, refrigerated at 2-8° C., and mixed for 6 hours. After the mixing was stopped, the precipitate was allowed to settle for 6 hours. If required, the pH was further adjusted to 6.0±0.1 at 2-8° C. using either 5.7 M sodium acetate or 1 N sodium hydroxide, followed by additional mixing for 1 hour and settling for 3 hours at room temperature (total mixing and settling time not to exceed 24 hours). After the settling is completed, the mixed egg white formed three layers, i.e., top, middle, and bottom layers. A tube was then placed into the middle layer and the middle layer was siphoned or pumped out through the tube without disturbing the top and bottom layers. Filters (sequential Pall Corporation depth filters, 40 micron, 3-6 micron, 0.1-0.3 micron, respectively) were pre-rinsed with 80 liters of purified water per meter squared of filter area to remove total organic carbon, leachables, and extractables, and then drained. The pre-rinsed filters were then treated with 1 filter hold up volume of a pre-treatment buffer solution containing 20 mM sodium phosphate and 140 mM sodium chloride at pH 6.0 and then drained. The egg white solution was decanted, avoiding the settled precipitated and aggregated egg white particulates, and filtered through dead end filtration at a flow rate of 1 liter per meter squared per filter type or a differential pressure less than 30 psid to remove any un-settled precipitated material and collected into a sterile single use mixer. At the completion of egg white filtration, the retained egg white in the filtration system was flushed with one filter train hold up volume of the pre-treatment buffer solution containing 20 mM sodium phosphate and 140 mM sodium chloride at pH 6.0 to recover product and collected in a sterile single use mixer. The filtered egg white solution was sampled for measurement of enzyme activity and ultraviolet (UV) absorbance and stored at 2-8° C. for up to 24 hours before it was used for isolation of recombinant proteins in the egg white via column chromatography. Table 1 shows the results of egg white acidification by using the acidic buffer described above (i.e., 5.7 M NaOAc, pH 4.0, and 1.3% wt/wt).

TABLE 1

|  | Average |
| --- | --- |
| Total Weight (kg) of the Mixed Egg White | 83.52 ± 2.03 |
| Native pH | 8.41 ± 0.06 |
| Native Conductivity (mS/cm) | 8.47 ± 0.25 |
| 5.7M NaOAc, pH: 4.0 (mL) | 1 ± 0.02 |
| %5.7M NaoAC added (w/w) | 1.30% |
| %5.7M NaOAc added (v/w) | 1.20% |

| Time Post Bolus Addition (min) | pH | Conductivity (mS/cm) |
| --- | --- | --- |
| 10 | 5.79 ± 0.03 | 9.52 ± 0.08 |
| 30 | 5.92 ± 0.02 | 9.45 ± 0.08 |
| 90 | 5.93 ± 0 | 9.48 ± 0.09 |
| 180 | 6.01 ± 0.01 | 9.48 ± 0.06 |
| 1080 | 6.09 ± 0.01 | 9.49 ± 0.09 |

Example 2

Method of Preparing Egg White for Bulk Chromatographic Processing without a Settling Step Four hundred kilograms of frozen egg white (+/−10%) of frozen egg white (−20° C.) was thawed at 2-8° C. (in a walk-in cold room) in approximately 24-72 hours. The thawed egg white was pooled into a jacketed single use closed mixing vessel and maintained at 2-8° C. An acidic buffer containing 5.7 M sodium acetate at pH 4.0 (1.08% wt/wt) was added to the thawed egg white at 1 kilogram per minute, ensuring that the duration of the addition of the acidic buffer did not exceed 5 minutes, to obtain a final target pH of 6.0±0.5. The acidified egg white solution was stirred continuously for 3 hours at 2-8° C. The acidified egg white was then warmed to 21±3° C. via the jacketed tank prior to filtration. Filters (sequential Pall Corporation depth filters, 40 micron, 3-6 micron, 0.1-0.3 micron, respectively) were pre-rinsed with 80 liters of purified water per meter squared of filter area to remove total organic carbon, leachables, and extractables. The purified water in the filter train was displaced with a pre-treatment buffer solution containing 20 mM sodium phosphate and 140 mM sodium chloride at pH 6.0 until the filter effluent conductivity was within the acceptable conductivity range of the pre-treatment buffer (e.g., 10-15 mS/cm). The homogeneously mixed acidified egg white was filtered through dead end filtration at a flow rate of 1 liter/min/m$^2$ per filter type or resulting in a differential pressure≤10 psi to remove any precipitated or aggregated material. The initial filter effluent volume equal to 80% of the filter train hold up volume was used to displace the pre-treatment buffer and was discarded prior to product collection. The remaining filtered pre-treatment buffer and egg white was collected into a sterile single use mixer. At the completion of egg white filtration, the retained egg white in the filtration system was flushed with 1.5 filter train hold up volumes (0.5 hold-up volumes are collected while 1 hold-up volume remains in the filtration train) of the pretreatment buffer solution containing 20 mM sodium phosphate and 140 mM sodium chloride at pH 6.0 to recover product and collected in the sterile single use mixing tank. The filtered egg white was sampled for measurement of enzyme activity and absorbance and stored at 2-8° C. for up to 24 hours before it is used for isolation of recombinant proteins in the egg white via column chromatography.

Example 3

Scale Down of Egg White Manufacturing Process to Evaluate Direct Loading on Depth Filtration Performance and Robustness of Egg White Acidification Materials All chemicals used for the Clarification studies were of USP/MC grade. Egg white source materials are listed in Table 2. All source material was stored at −20° C. and thawed at 2-8° C. 48-72 hours prior to use. Source material was pooled and maintained at 2-8° C. up through the acidification step.

TABLE 2

| Egg White Source Materials | | | |
| --- | --- | --- | --- |
| Run | Egg White Aliquot (L) | Titer (g/L)* | Zygosity |
| 1 | 20 | 0.77 | Homo |
| 2 | 20 | 1.02 | Homo |
| 3 | 20 | 0.79 | Homo |

*Based on enzymatic activity

For all buffer preparations, conductivity measurements were conducted utilizing pH/conductivity meters with temperature compensated to 25° C. pH of buffers were measured at 20° C. In-process buffer preparation formulations are listed in Table 3 below.

TABLE 3

Buffer Formulation

| Buffer | | Raw Material | g/L | Specifications pH | Cond (mS/cm) |
|---|---|---|---|---|---|
| Egg White Acidification | 5.7M Sodium Acetate, pH 4.0 | Sodium Acetate Trihydrate | 136.1 | 4.0 ± 0.1 | 36.0 ± 5.0 |
| | | Glacial Acetic Acid | 285.0 | | |
| Filter Flush/ Equilibration | 20 mM Sodium Phosphate, 140 mM NaCl, pH 6.0) | $NaH_2PO_4 \cdot H_2O$ $Na_2HPO_4 \cdot 7H_2O$ NaCl | 2.24 1.02 8.18 | 6.0 ± 0.1 | 16.0 ± 2.0 |
| Wash 1 | 5 mM Sodium Phosphate, pH 6.0 | $NaH_2PO_4 \cdot H_2O$ $Na_2HPO_4 \cdot 7H_2O$ | 2.24 1.02 | 6.0 ± 0.1 | 0.45 ± 0.15 |
| Wash 2 | 5 mM Tris, 1M NaCl, pH 7.2 | Tris Base NaCl | 0.61 58.44 | 7.2 ± 0.1 | 88.0 ± 5.0 |
| Wash 3 | 5 mM Tris, 0.25M NaCl, pH 7.2 | Tris Base NaCl | 0.61 14.61 | 7.2 ± 0.1 | 23.0 ± 3.0 |
| Elution | 5 mM Tris, 17% IPA, pH 7.2 | Tris Base Isopropyl Alcohol | 0.61 133.0 | 7.2 ± 0.1 | <2.0 |
| Acid Cleaning | 0.85% Phosphoric Acid | Phosphoric Acid | 16.9 | N/A | N/A |

Process Equipment

Process skids (AKTA Explorers) were serviced (preventive maintenance) by GE healthcare. Process equipment (Pall Stax chassis and AKTA Explorers) was maintained by Synageva PD personnel during the entire characterization study. Table 4 below lists all hardware equipment used in this Example.

TABLE 4

Equipment List

| Step | Equipment Description | Manufacture | Part No. |
|---|---|---|---|
| General | Accumet XL550 pH/conductivity meter | Fisher Scientific | X13-12005 |
| | 3.2 kg Bench Scale | Mettler Toledo | ML3002E |
| | 50 kg Floor Scale | Ohaus | CD-33 |
| | Masterflex L/S Pump (10-600 rpm) | Cole-Parmer | 7523-60 |
| | Masterflex I/P 73 C-flex | Cole Parmer | 06427-73 |
| | Masterflex L/S 24 Bioprene | Cole Parmer | 06508-24 |
| Clarification | Stax Pilot Chassis | Pall | SXLSC02W |
| | Stax Pilot Chassis | Pall | SXLSC02W |
| | Masterflex I/P Pump (33-600 rpm) | Cole-Parmer | 77410-10 |
| | Pressure Flow Cell | SciLog | 080-696-PSX-5 |
| | SciPres Pressure Monitor | SciLog | 080-690 |
| | 250 kg Floor Scale | Ohaus | CD-33 |
| PHIC SDM | AKTA Explorer | GE Healthcare | 29001622 |
| | XK16 Column | GE Healthcare | N/A |
| A280 | Nanodrop 2000 | Thermo Scientific | N/A |
| SDS-PAGE | Mini-PROTEAN TGX 4%-20% | Bio-Rad | 456-1096 (L/N: 400091244) |
| | Precision Plus Dual Color Standards | Bio-Rad | 161-0374 (L/N: 35001785) |
| | Mini PROTEAN Tetra Cell | Bio-Rad | 165-8000 |

Pall STAX chassis (PN# SXLSC02W) were set up using the STAX depth filters listed in Table 5 in the following configuration (40 μm, 3-6 μm, and 0.1-0.3 μm) and an additional Sartobran P 0.2 μm filter.

Chassis #1: (bottom) Manifold→T2600→Vent plate (top)

Chassis #2: (bottom) Manifold→K200P→Vent plate→Manifold→Bio10→Vent plate (top)

Each filter was sandwiched in between a 1.5" inlet/outlet manifold (P/N: 7008225) and a top Vent plate. Hold up volume of each individual filter was determined empirically during the initial water flush.

TABLE 5

Depth Filtration Equipment

| Run | Filter | Load Ratio (L/m²) | Pore Size (um) | Stax Filters (S.A. m²) | Hold Up Vol (L) |
|---|---|---|---|---|---|
| 1 | T2600 | 20 | 40 | 1.0 | 6.5 |
| | K200P | 20 | 3-6 | 1.0 | 6.0 |
| | BIO10 | 20 | 0.1-0.3 | 1.0 | 5.5 |
| | Sartobran P | 160 | 0.22 | 1.8 | 1.35 |
| 2 | T2600 | 20 | 40 | 1.0 | 6.5 |
| | K200P | 20 | 3-6 | 1.0 | 6.0 |
| | BIO10 | 40 | 0.1-0.3 | 0.5 | 3.8 |
| | Sartobran P | 160 | 0.22 | 1.8 | 1.35 |
| 3 | T2600 | 20 | 40 | 1.0 | 6.5 |
| | K200P | 20 | 3-6 | 1.0 | 6.0 |
| | BIO10 | 40 | 0.1-0.3 | 0.5 | 4.0 |
| | Sartobran P | 160 | 0.22 | 1.8 | 1.35 |

Columns XK 16/20 (GE Healthcare) were used for all phenyl hydrophobic interaction chromatography (PHIC) column packing. All chromatography was performed on an AKTA Explorer equipped with Unicorn software version 5.31 (GE Healthcare).

Procedures

Before starting the clarification step, frozen egg white aliquots (totaling 20 L) were thawed for 2-8° C. for 48-72 hours. The thawed egg white was pooled into an appropriately sized polypropylene tank (25 L) with sterile media liner (Thermo Scientific/Hyclone P/N 343050-0005). The pooled egg white was mixed to homogeneity using an overhead mixer (330 rpm) at 2-8° C. The pooled egg white was then conditioned to the target pH through addition of 5.7 M sodium acetate at pH 4.0. Table 6 lists the volume of the 5.7 M sodium acetate added for each clarification run to achieve the target pH. The pH was monitored for more than 2 hours to ensure target pH was achieved.

TABLE 6

Pooled Egg White Acidification

| Run | Pool Vol. (L) | Target pH | 5.7M Acetate Vol. (mL) | 5.7M Acetate (% wt/wt) | 5.7M Acetate (% v/v) | Initial pH | Final pH | Acidification Time (h) |
|---|---|---|---|---|---|---|---|---|
| 1 | 20 | 6.0 | 180 | 0.94 | 0.90 | N/A | 5.94 | 18 |
| 2 | 20 | 5.7 | 245 | 1.27 | 1.22 | 8.11 | 5.67 | 24 |
| 3 | 20 | 6.3 | 164 | 0.83 | 0.80 | 8.21 | 6.25 | 6 |

Prior to filtration, filters were flushed individually with 80 L/m$^2$ with filtered RO/DI water. During the water flush, the holdup volume for each filtered was empirically determined. Upon completion of the water flush, the filters were plumbed into a continuous train and flushed with 16 L/m$^2$ of PHIC equilibration buffer (20 mM sodium phosphate, 140 mM sodium chloride, pH 6.0). Buffer flush ended when pH and conductivity of the effluent met flush buffer specifications (e.g., pH 6.0±0.1, conductivity 16.0±2.0). Pooled egg white was loaded onto the filter train using a ⅜" dip tube (I/P 73 tubing Cole) at 1.0 L/min with continuous mixing (overhead mixer, 300 rpm). 80% of the measured, cumulative hold up volume (~13.2 L) was collected and directed to waste. Filtrate was then collected in a separate appropriately sized container until the congealed low density precipitate entered dip tube. Filtration train was then flushed with 1.5 hold up volumes (~25 L) with a buffer equilibration buffer. The final filtrate was mixed well using a clean tank paddle to ensure homogeneity prior to sampling. Filtrate was stored at 2-8° C. overnight prior to PHIC separation.

Prior to PHIC separation, filtrate stored at 2-8° C. was warmed using a room temperature water bath. The filtrate was secondarily filtered through a Sartobran 150 cartridge (0.45 um/0.22 um, P/N 5231307H4-00) to generate the final PHIC load. Table 7 lists the buffers and in-process parameters used.

TABLE 7

PHIC Chromatography Unit Operation Steps

| Step | Buffer | CV | Linear Velocity (cm/h) | Flow Rate (mL/min) |
|---|---|---|---|---|
| Equilibration | 20 mM Sodium Phosphate, 140 mM NaCl, pH 6.0 | 5 | 120 cm/h | 4.02 |
| Loading |  |  | 60 cm/h | 2.01 |
| Wash 1 | 5 mM Sodium Phosphate, pH 6.0 | 8 | 120 cm/h | 2.01 (1CV) 4.02 (7CV) |
| Wash 2 | 5 mM Tris, 1M NaCl, pH 7.2 | 8 | 120 cm/h | 4.02 |
| Wash 3 | 5 mM Tris, 0.25M NaCl, pH 7.2 | 4 | 120 cm/h | 4.02 |
| Pre-Elution | 5 mM Tris, 17% IPA, pH 7.2 | UV → 40 mAU | 120 cm/h | 4.02 |
| Fraction 1 | 5 mM Tris, 17% IPA, pH 7.2 | UV → 800 mAU | 120 cm/h | 4.02 |
| Elution | 5 mM Tris, 17% IPA, pH 7.2 | 1.9 | 120 cm/h | 4.02 |
| Post Elution | 5 mM Tris, 17% IPA, pH 7.2 | 2.0 | 120 cm/h | 4.02 |
| Strip | RO/DI | 5 | 60 cm/h Upflow | 2.01 |
| Acid Cleaning | 0.85% Phosphoric Acid | 3 | 60 cm/h Upflow | 2.01 |
| Water Rinse | RO/DI | 5 | 60 cm/h Upflow | 2.01 |
| CIP | 0.5N NaOH | 3 | 60 cm/h Upflow (1 h hold) | 2.01 |
| Water Rinse | RO/DI | 5 | 60 cm/h Upflow | 2.01 |
| Storage | 20% Ethanol | 3 | 60 cm/h Upflow | 2.01 |

Results and Discussion
(1) Direct Loading of Acidified Egg White (i.e., No Settling Step)

Initially, a single center point run ("Run 1"; 1:20 scale; 20 L acidified egg white at pH of about 6) was conducted to evaluate the impact of direct loading (no settling, loading ration of 20 L/m$^2$) on depth filtration performance in order to establish a representative experimental scale model. For each filter (i.e., T2600, K200P, Bio10), although the inlet feed pressure in the filter did increase linearly over the course of acidified egg white loading, the differential pressure did not exceed 10 psid. In addition, feed pressure did not increase further during the buffer flush and exhibited a dramatic decrease in filter T2600. These results suggest that direct loading of the acidified egg white to the filters did not significantly block the filters during this run.

The protein recovery results are summarized in Table 8 below. As shown in Table 8, protein recovery after the clarification step met target expectation (>70%).

TABLE 8

Protein Recovery After Clarification

| Run 1 | Ave. Adj results (U/mL) | Volume (mL) | Recovered Protein (mg) |
|---|---|---|---|
| Egg White Pool | 199.5 | 20000 | 15344.6 |
| Acidified Egg White Pool | 253.4 | 20000 | 19493.6 |
| Clarified Egg White Pool | 122.8 | 32700 | 15438.2 |
| Clarif Step Yield* (Thawed Egg White) | | | 100.6% |
| Clarif Step Yield* (Acidified Egg White) | | | 79.2% |

*Based on Enzymatic Activity

PHIC column performance of Run 1 was comparable to the results obtained from runs including a settling step of the acidified egg white. In addition, protein purity was measured by a SDS-PAGE analysis using 4-20% Tris-Glycine gel. PHIC eluent fractions from Run 1 did not reveal any differences in banding pattern when compared to runs including a settling step. These data suggested that direct loading of acidified egg white during clarification (i.e., filtration) did not impact protein recovery or PHIC performance in terms of yield and purity.

The above results suggest that acidified egg white can be directly loaded to the filters during the clarification step without going through a settling step. This method was then applied to the Robustness study runs (i.e., Runs 2 and 3) described in the next section.

(2) Robustness of Egg White Acidification

A 2-factor, 2-level experimental design (high/low, low/high) was used to evaluate the robustness of the egg white acidification step. The experimental conditions are defined in Table 6. In Run 2, acidification was performed for 24 hours to achieve a final pH of 5.67 (i.e., about 5.7). In Run 3, acidification was performed for 6 hours to achieve a final pH of 6.25 (i.e., about 6.3). The results show that both runs exhibited comparable linear feed pressure increases and maximum feed pressures due to increased T2600 fouling. A lower maximum feed pressure was observed in Run 2, which is believed to be due to a correlation between egg white pH and egg white viscosity (i.e., lower egg white pH resulting in lower egg white viscosity). In no case did the feed pressure exceed 10 psig, showing comparable performance to Run 1.

After the clarification step, the protein recoveries in Runs 2 and 3 respectively were 71% and 83%, which met target expectations of (i.e., ≥70%) and were comparable to Run 1 (i.e., 79%). After PHIC separation, the protein yields in Runs 2 and 3 respectively were 59% and 68%, which were comparable to those obtained from runs including a settling step. Chromatogram overlays comparing Runs 2 and 3 to both Run 1 confirmed comparable column performance.

The above results suggest that variation of acidification pH and time did not result in any significant negative impact relative to enzyme activity or yield. Thus, the clarification step was robust when conducted within two tested ranges (i.e., acidification pH 5.7-6.3 and acidification time of 6-24 hours).

(3) Egg White in-Process Stability

Process hold studies were conducted to define maximum hold times for the following three unit operation hold points: (1) thawed egg white (2-8° C.), (2) acidified egg white (2-8° C. and ambient temperature), and (3) clarified egg white (2-8° C. and ambient temperature). Stability of the product (in terms of enzymatic activity) was assessed over a 72-96 hour time period. Two separate stability studies were conducted to assess impact on clarification parameter variance on product hold times at the acidified and clarified egg white steps. Sixty mL aliquots (two for each of acidified and clarified egg white) were taken from each of the two robustness experiments above (i.e., Runs 2 and 3) and stored at either 2-8° C. or ambient temperature. 1.5 mL samples were taken every 24 hours up to either 72 hours (pH 5.7/24 hours) or 96 hours (pH 6.3/6 hours). Due to time constraints, a stability study was not conducted on Run 1 (center point). The stability design parameters are summarized in Table 9 below.

TABLE 9

In Process Stability Design

| | | | Study Parameters | | | |
|---|---|---|---|---|---|---|
| Hold Point | Commercial Process Target (hr) | Commercial Hold Temp (° C.) | Study Temp (° C.) | pH | Acidification Time (h) | Hold Time (h) |
| Thawed egg white | 72-96 | 2-8 | 2-8 | N/A | N/A | 0-168* |
| | | | 2-8 | N/A | N/A | |
| Acidified egg white | 6 hr (6-24 hr range) | 2-8 | 2-8 | 5.7-6.3 | 6-24 | 0-72 (24 h) |
| | | | RT** | | | 0-96 (6 h) |
| Clarified egg white | ≤6 hr (no refiltration) ≤24 hr (with refiltration) | RT or 2-8 | 2-8 | 5.7-6.3 | 6-24 | 0-72 (24 h) |
| | | | RT** | | | 0-96 (6 h) |

*T = 0 equals the beginning of the Thaw (additional hold time including thaw time)
**RT = 18-25° C. (Average: 22° C.)

The results show that enzymatic activity for all three in-process hold points (thawed, acidified, and clarified egg white) was stable over the entirety of the time course study (up to 96 hours) at 2-8° C. In addition, variation of either the acidification pH or acidification time in general did not negatively impact enzymatic activity. A single set of test parameters (pH 5.7, room temperature) for the acidified egg white hold point did exhibit a ~20% decrease in enzymatic activity. However, the current commercial process storage target for the acidified egg white is 2-8° C. and, therefore, this observation is not a risk to the commercial process. Based on the data, the thawed/pooled egg white was stable for up to 168 hours (including the initial 72 hour thaw time) at 2-8° C., the acidified egg white was stable up to 96 hours at 2-8° C., and the clarified egg white stage was stable up to 96 hours at 2-8° C. or room temperature.

(4) Supplemental DNA Clearance Study

Although egg white itself does not contain DNA, the egg white harvesting process may result in the presence of host genomic DNA through the introduction of minor amounts egg yolk into the egg white pool. Acidified and clarified egg white derived from the studies of Runs 1-3 above were analyzed for host genomic DNA. The analyses revealed the following:

1. DNA was detected in the pooled and acidified egg white
2. Significant DNA clearance during the Clarification step was identified.

These data suggested that in addition to egg white host protein clearance, the clarification step provides a means to remove host genomic DNA from the product pool.

Other embodiments are within the scope of the following claims.

What is claimed is:

1. A method of preparing egg white for bulk chromatographic processing, the method comprising the steps of:
    adding an acidic buffer comprising an acidic agent to a pool of egg white, the acidic buffer being from about 0.5 wt % to about 5 wt % per kilogram of the egg white;
    mixing the acidic buffer and the egg white to form a mixed egg white having a pH from about 5 to about 6.5; and
    allowing the mixed egg white to settle such that the egg white separates into top, middle and bottom layers.

2. The method of claim 1, wherein the acidic agent is selected from the group consisting of acetic acid, hydrochloric acid, sulfuric acid, nitric acid, phosphoric acid, hydrofluoric acid, hydrobromic acid, perchloric acid, citric acid, boric acid, tartaric acid, lactic acid, formic acid, oxalic acid, uric acid, and barbituric acid.

3. The method of claim 2, wherein the acidic buffer further comprises from about 5M to about 6M sodium acetate.

4. The method of claim 3, wherein the acidic buffer comprises about 5.7 M sodium acetate.

5. The method of claim 1, wherein the acidic buffer is from about 0.5 wt % to about 2wt % per kilogram of the egg white.

6. The method of claim 5, wherein the acidic buffer is from about 0.7 wt % to about 1.5 wt % per kilogram of the egg white.

7. The method of claim 6, wherein the acidic buffer is from about 0.9 wt % to about 1.4 wt % per kilogram of the egg white.

8. The method of claim 1, wherein the acidic buffer has a pH from about 4 to about 6.5.

9. The method of claim 8, wherein the acidic buffer has a pH about 4.

10. The method of claim 8, wherein the acidic buffer has a pH about 4.5.

11. The method of claim 1, wherein the pH of the mixed egg white is from about 5 to about 6.3.

12. The method of claim 11, wherein the pH of the mixed egg white is from about 5.7 to about 6.3.

13. The method of claim 12, wherein the pH of the mixed egg white is from about 5.8 to about 6.2.

14. The method of claim 13, wherein the pH of the mixed egg white is from about 5.9 to about 6.1.

15. The method of claim 14, wherein the pH of the mixed egg white is about 6.

16. The method of claim 1, wherein the pH of the mixed egg white is a value such that the mixed egg white is rendered least viscous.

17. The method of claim 1, wherein the egg white is mixed for at least about 1 hour.

18. The method of claim 1, wherein the egg white is mixed at a temperature from about 2° C. to about 25° C.

19. The method of claim 1, wherein the egg white pool has a volume of at least about 10 liters.

20. The method of claim 1, wherein the acidic buffer is added to the egg white pool in a single bolus injection.

21. The method of claim 20, wherein the acidic buffer is added at a rate of at least about 1 L/minute.

22. The method of claim 1, wherein the addition of the acidic buffer and the mixing of the egg white are performed concurrently.

23. The method of claim 1, further comprising a step of isolating the middle layer.

24. The method of claim 23, further comprising filtering the middle layer after the isolation step.

25. The method of claim 24, wherein the filtering comprises passing at least a portion of the middle layer through a filter having an average pore size ranging from about 0.1 μm to about 100 μm.

26. The method of claim 24, wherein the filtering comprises passing at least a portion of the middle layer through a plurality of filters.

27. The method of claim 1, further comprising filtering the mixed egg white without allowing the mixed egg white to settle.

28. The method of claim 27, wherein the filtering step comprises filtering the mixed egg white through a filter having an average pore size ranging from about 0.1 μm to about 100 μm.

29. The method of claim 28, wherein the filtering step comprises one or more subsequent filtering steps following an initial filtering of the mixed egg white, the one or more subsequent filtering steps using one or more filters having an average pore size ranging from about 0.1 μm to about 40 μm.

30. The method of claim 1, further comprising a centrifugation step after the mixing step, wherein the mixed egg white is centrifuged to separate precipitates comprising ovomucin-lysozyme complexes from supernatant.

31. The method of claim 1, wherein the egg white comprises a recombinant therapeutic protein exogenous to egg white.

32. A method of isolating a recombinant protein from egg white, comprising the steps of:
    providing a pool of egg white comprising a recombinant protein, the pool having a volume of at least about 10 liters;
    adjusting the pH of the egg white to from about 5 to about 6.5, wherein the conductivity of the pH-adjusted egg white is from about 8 mS/cm to about 20 mS/cm;
    allowing the egg white to settle such that the pH-adjusted egg white separates into top, middle and bottom layers;
    filtering at least a portion of the middle layer of the pH-adjusted egg white to form a solution; and
    isolating the recombinant protein in the egg white by column chromatography.

33. The method of claim 32, wherein the filtering step comprises passing at least a portion of the middle layer through a filter having an average pore size from about 0.1 μm to about 100 μm.

34. The method of claim 32, wherein the adjusting step comprises mixing the egg white with an acidic buffer.

35. The method of claim 32, wherein the acidic buffer has a conductivity from about 8 mS/cm to about 40 mS/cm.

36. The method of claim 32, wherein the acidic buffer is from about 0.5 wt % to about 5 wt % per kilogram of the egg white.

37. The method of claim 1, further comprising the steps of:
passing a pre-treatment buffer having a conductivity between about 8 mS/cm and about 20 mS/cm through a filter; and
passing at least a portion of the middle layer of the mixed egg white through the filter to obtain a filtered egg white.

38. The method of claim 37, wherein the pre-treatment buffer has a pH substantially the same as the pH of the egg white.

39. The method of claim 38, wherein the pre-treatment buffer has a pH from about 5.9 to about 6.1.

40. The method of claim 38, wherein the pre-treatment buffer has a pH of about 6.

41. The method of claim 37, wherein the pre-treatment buffer comprises sodium phosphate and sodium chloride.

42. The method of claim 37, wherein the pre-treatment buffer has a conductivity from about 10 mS/cm to about 18 mS/cm.

43. The method of claim 37, wherein the at least a portion of the middle layer of the mixed egg white has a conductivity from about 8 mS/cm to about 20 mS/cm.

44. The method of claim 37, wherein the filter has a filtration medium area of at least about 8 m2.

45. The method of claim 37, wherein the filter has an average pore size from about 0.1 μm to about 100 μm.

46. The method of claim 37, wherein the at least a portion of the middle layer of the mixed egg white has a volume of at least about 50 L.

47. The method of claim 37, wherein the at least a portion of the middle layer of the mixed egg white is passed through the filter under a differential pressure less than about 30 psi.

48. The method of claim 47, wherein the at least a portion of the middle layer of the mixed egg white is passed through the filter under a differential pressure less than about 15 psi.

* * * * *